US011369273B2

(12) United States Patent
Imai et al.

(10) Patent No.: US 11,369,273 B2
(45) Date of Patent: Jun. 28, 2022

(54) GUIDEWIRE CONNECTOR AND ULTRASONIC IMAGING APPARATUS

(71) Applicant: Hitachi, Ltd., Tokyo (JP)

(72) Inventors: Ryo Imai, Tokyo (JP); Tomohiko Tanaka, Tokyo (JP)

(73) Assignee: FUJIFILM Healthcare Corporation, Kashiwa (JP)

( * ) Notice: Subject to any disclaimer, the term of this patent is extended or adjusted under 35 U.S.C. 154(b) by 256 days.

(21) Appl. No.: 16/883,335

(22) Filed: May 26, 2020

(65) Prior Publication Data

US 2021/0015369 A1    Jan. 21, 2021

(30) Foreign Application Priority Data

Jul. 18, 2019   (JP) .............................. JP2019-132535

(51) Int. Cl.
*A61B 5/00*      (2006.01)
*G02B 6/38*      (2006.01)
*G02B 6/42*      (2006.01)

(52) U.S. Cl.
CPC .......... *A61B 5/0095* (2013.01); *G02B 6/3825* (2013.01); *G02B 6/4204* (2013.01)

(58) Field of Classification Search
CPC ... A61B 5/0095; G02B 6/3825; G02B 6/4204
USPC ....................................................... 600/407
See application file for complete search history.

(56) References Cited

U.S. PATENT DOCUMENTS

| | | | | |
|---|---|---|---|---|
| 4,850,351 A | * | 7/1989 | Herman | A61B 18/245 606/7 |
| 5,427,118 A | * | 6/1995 | Nita | A61B 17/22012 600/585 |
| 5,454,373 A | * | 10/1995 | Koger | A61B 8/4461 600/463 |
| 2005/0232550 A1 | * | 10/2005 | Nakajima | G02B 6/3898 385/60 |
| 2007/0232893 A1 | * | 10/2007 | Tanioka | A61B 5/02007 600/407 |
| 2009/0030312 A1 | * | 1/2009 | Hadjicostis | A61B 8/4488 606/33 |
| 2011/0144502 A1 | * | 6/2011 | Zhou | A61B 5/0095 600/463 |
| 2012/0316433 A1 | * | 12/2012 | Maruyama | A61B 1/00087 600/478 |
| 2014/0180056 A1 | * | 6/2014 | Hoseit | A61B 5/6852 600/407 |

(Continued)

FOREIGN PATENT DOCUMENTS

JP         5819387 B2    11/2015
JP         6470762 B2     2/2019

*Primary Examiner* — Dalzid E Singh
(74) *Attorney, Agent, or Firm* — Crowell & Moring LLP

(57) ABSTRACT

Provided is a guidewire connector that does not interfere with an introduction of another in-body insertion instrument and is capable of maintaining cleanliness of the guidewire when connecting a guidewire mounted with a photo-acoustic ultrasonic wave generator. The guidewire connector according to the present disclosure includes an adapter member detachably attached to an light emitting apparatus, and a wire fixing member attaching the guidewire to the adapter member, in which the wire fixing member has an outer diameter equal to or smaller than an outer diameter of the guidewire.

14 Claims, 10 Drawing Sheets

(56) References Cited

U.S. PATENT DOCUMENTS

| | | | |
|---|---|---|---|
| 2015/0297092 A1* | 10/2015 | Irisawa | A61B 17/3403 |
| | | | 600/407 |
| 2016/0310041 A1* | 10/2016 | Jenkins | A61B 5/6851 |
| 2017/0082806 A1 | 3/2017 | Van Der Mark et al. | |
| 2017/0128090 A1* | 5/2017 | Sarge | A61F 2/958 |
| 2018/0164510 A1* | 6/2018 | Shouda | G02B 6/4292 |
| 2020/0036133 A1* | 1/2020 | Komatsubara | G02B 6/36 |

* cited by examiner

<BEFORE CONNECTION>

<AFTER CONNECTION>

<BEFORE CONNECTION>

<AFTER CONNECTION>

<BEFORE CONNECTION>

<AFTER CONNECTION>

<BEFORE CONNECTION>

<AFTER CONNECTION>

GUIDEWIRE CONNECTOR AND ULTRASONIC IMAGING APPARATUS

CROSS-REFERENCE TO RELATED APPLICATION

This application claims the priority of Japanese Patent Application No. 2019-132535 filed Jul. 18, 2019, which is incorporated herein by reference in its entirety.

BACKGROUND OF THE INVENTION

1. Field of the Invention

The present disclosure relates to a connector for a guidewire housing an optical waveguide therein.

2. Description of the Related Art

There is a treatment method for performing treatment in a body in a minimally invasive manner using a small-diameter treatment instrument such as a catheter. In such treatment, although the treatment instrument is put into the body by inserting a needle or the like into a body surface such that burden on a patient is smaller than that in laparotomy and thoracotomy surgeries, it is necessary to obtain an image of a treatment site with a device for imaging an inside of the body since the treatment instrument cannot be seen directly. As an example of such minimally invasive treatment, there is a method of treating stenosis and occlusion sites of a blood vessel with an instrument such as a catheter. In order to specify a position of the instrument during treatment, an X-ray imaging device capable of obtaining a living body radiographic image in a wide range is widely used. On the other hand, there are problems that, in X-ray imaging, body tissues other than bones are hardly reflected and it is necessary to use a contrast agent in combination, only an area where blood flow exists can be imaged with the contrast agent, and an occlusion portion itself cannot be imaged. Therefore, ultrasonic imaging is sometimes used as a supplement. The ultrasonic imaging can draw blood vessels or the like without the contrast agent, and does not expose the blood vessels.

In the examination and treatment using an ultrasonic guide as described above, an affected portion or a vicinity of a small-diameter medical instrument is drawn, and the examination and treatment instrument is advanced based on the image. In the treatment using the catheter or the like, a blood vessel in a vicinity of a stenosis and occlusion site is drawn, and the instrument is advanced to be prevented from getting out of the blood vessel. However, in the examination and treatment using the ultrasonic guide, there are problems that the instrument may get out of an ultrasonic image capturing area, and it may be difficult to distinguish a tip end portion of the catheter and the like on the image.

As a method capable of solving the above problems, a technique for supporting an operation of an operator has been devised in which an ultrasonic wave is generated from an instrument, a position of the instrument is determined by using the ultrasonic wave as a signal for detecting the position, and displaying the position of the instrument on an ultrasonic image (Japanese Patent No. 5819387 (PTL 1)). In the technique, acquisition of the ultrasonic image and acquisition of the signal from an ultrasonic wave generating source are alternately repeated to draw the position of the instrument on the ultrasonic image.

A guidewire used in catheter treatment is an instrument used to assist in an introduction of a treatment instrument, such as other catheters. In such a treatment machine, an optical fiber may be connected to the guidewire by, for example, extending the optical fiber from the ultrasonic imaging apparatus and using an optical fiber connector as an intermediate member. Japanese Patent No. 6470762 (PTL 2) describes an example of such an optical fiber connector.

The position of the instrument in a body cavity can be acquired by inserting the guidewire into the body cavity of a subject and outputting the ultrasonic wave from an ultrasonic oscillator disposed at a tip end of the guidewire. A source using a photo-acoustic effect is useful as such an ultrasonic transmission source. In PTL 1, an ultrasonic transmission source using the photo-acoustic effect is used.

When an optical fiber connector is configured as an intermediate member between an optical fiber and a guidewire, the optical fiber and the guidewire can be connected by connecting the optical fiber and the guidewire to both ends of the optical fiber connector respectively by using, for example, a member such as a ferrule.

On the other hand, it is considered that the optical fiber connector may be disposed at a tip end part of the guidewire, and the device and the guidewire may be connected by fitting the connector to the ultrasonic imaging apparatus. However, since the guidewire is a member for guiding another catheter, the other catheter is introduced into the body cavity adjacent to the guidewire. Therefore, it is necessary for the optical fiber connector at the tip end of the guidewire not to interfere with the introduction of the other catheter. A similar restriction exists when an instrument other than the catheter is introduced. The optical fiber connector described in PTL 2 does not particularly consider such a constraint condition.

Since the guidewire is inserted into the body cavity, it is necessary to keep the guidewire clean at all times. On the other hand, since the ultrasonic imaging apparatus is not necessarily clean, a distal end portion of the guidewire may not be clean when connecting the optical fiber connector to the device.

SUMMARY OF THE INVENTION

The disclosure has been made in view of the above problems, and an object of the disclosure is to provide a guidewire connector that can maintain cleanliness of a guidewire while not interfering with the introduction of another in-body insertion instrument when connecting a guidewire mounted with a photo-acoustic ultrasonic wave generator.

A guidewire connector according to the disclosure includes an adapter member that is detachably attached to a light emitting apparatus, and a wire fixing member that attaches the guidewire to the adapter member, in which the wire fixing member has an outer diameter equal to or smaller than an outer diameter of the guidewire.

According to the guidewire connector according to the disclosure, introduction can be prevented from being inhibited when another instrument is introduced from the distal end portion of the guidewire by a fixing mechanism having an outer diameter equal to or smaller than an outer diameter of the guidewire. Cleanliness of the guidewire can be kept since the guidewire connector can be disposable by a detachable adapter member.

DESCRIPTION OF THE PREFERRED EMBODIMENTS

Related Art

In order to facilitate understanding of the disclosure, a general configuration of a connecting member for connecting an ultrasonic imaging apparatus to an optical fiber connector will be described first, and restriction matters relating to the guidewire will be described.

Figure 1:
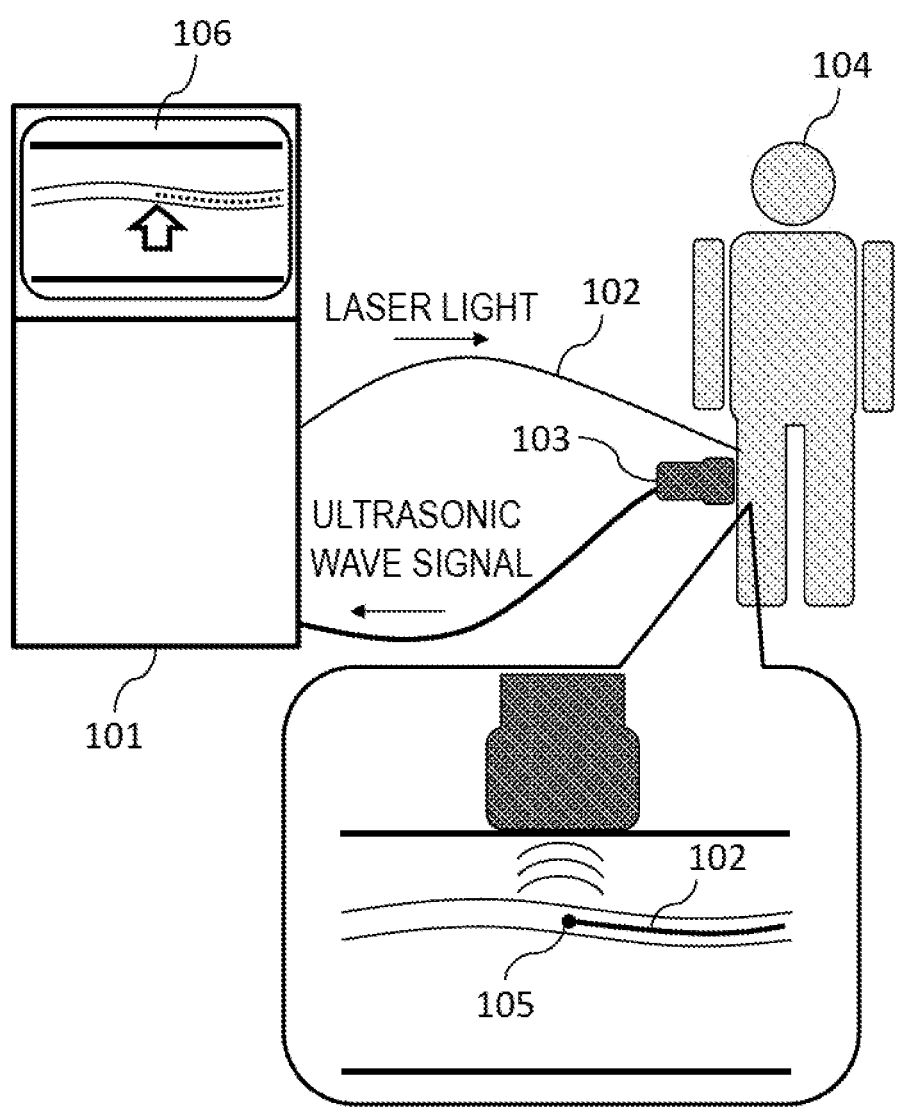
FIG. 1 is a schematic diagram of a guidewire based position detection system.

FIG. 1 is a schematic diagram of a guidewire based position detection system. The position detection system includes an ultrasonic imaging apparatus 101 and a guidewire 102 connected thereto. The ultrasonic imaging apparatus 101 acquires an ultrasonic image around an affected portion by an ultrasonic probe 103. The guidewire 102 is inserted into a subject 104, and oscillates ultrasonic wave by an ultrasonic oscillator 105. The ultrasonic probe 103 detects the ultrasonic wave, and the ultrasonic imaging apparatus 101 uses the ultrasonic wave to specify the position of the guidewire 102 in a body cavity. A tomographic image around the affected portion and a position of the guidewire 102 specified by a signal from the ultrasonic oscillator 105 are superimposed and displayed on a display 106.

In such a technique, it is necessary to install an ultrasonic wave generating source inside the guidewire 102, for example, having a diameter of 1 mm or less. Therefore, a technique of generating an ultrasonic wave by an optical fiber having a diameter of several hundreds μm or less and a light absorbing material attached to a tip end portion using a photo-acoustic effect is promising as the ultrasonic wave generating source. The photo-acoustic effect is an effect that, when a short pulse laser is emitted to a light absorbing material, a rapid temperature rise occurs locally, and an ultrasonic wave is generated by thermal expansion due to the temperature rise. PTL 1 also uses the photo-acoustic effect for generating an ultrasonic wave.

When an ultrasonic wave using the photo-acoustic effect is generated using the optical fiber and the light absorbing material as described above, it is necessary to introduce pulsed laser light for generating an ultrasonic wave into the optical fiber. Since the guidewire 102 is an instrument to be inserted into a human body, the guidewire 102 is used for treatment in a sterilized state from a viewpoint of cleanliness, and is basically disposable. On the other hand, the ultrasonic imaging apparatus 101 (or a laser light source) is not disposable, while in use, the guidewire 102 is used by connecting to a laser light source inside the ultrasonic imaging apparatus 101, and after use, the guidewire 102 is removed and discarded.

Figure 2:
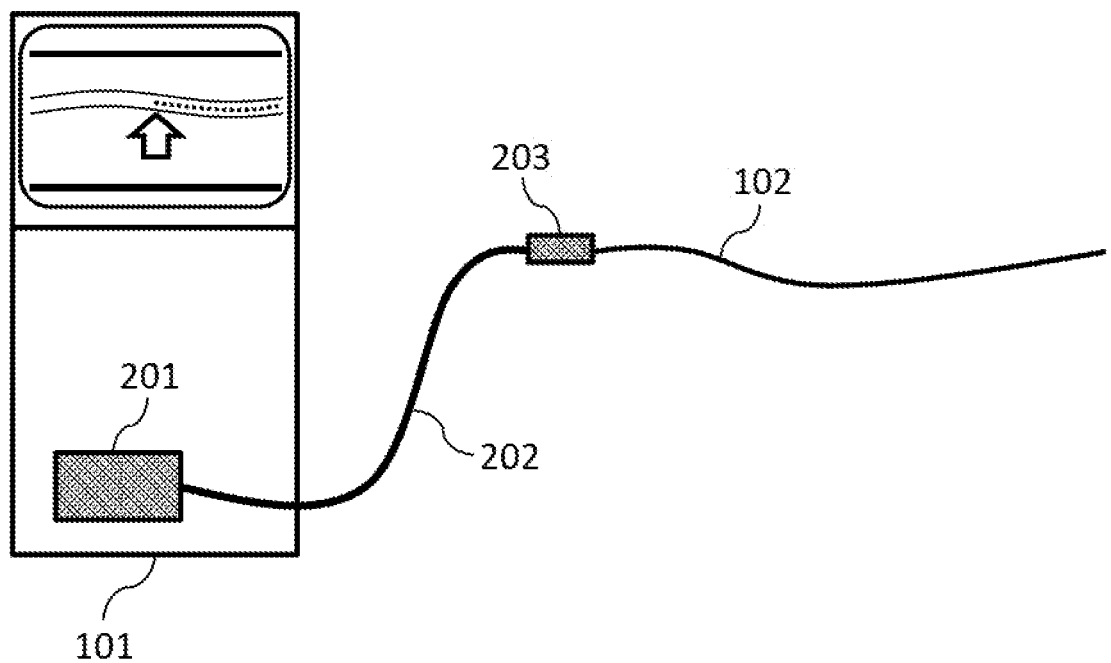
FIG. 2 shows one example of a mechanism for connecting a light source to a guidewire.

FIG. 2 shows one example of a mechanism for connecting the light source and the guidewire. In the example, a laser light source 201 is stored inside the ultrasonic imaging apparatus 101, and the laser light is transmitted to a connection unit 203 by an optical fiber 202. The laser light is supplied to the guidewire 102 by connecting the guidewire 102 to the connection unit 203. The optical fiber 202 and the optical fiber inside the guidewire 102 are connected to each other in the connection unit 203. In such a case, an optical fiber connector is generally used as the connection unit 203.

Figure 3:
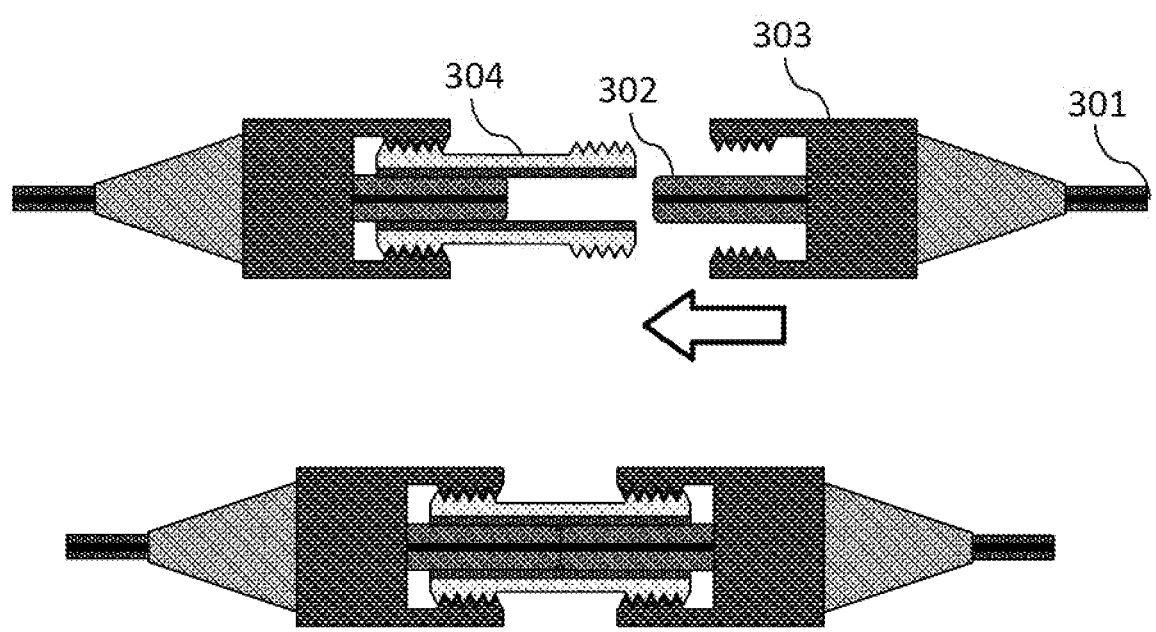
FIG. 3 is a schematic view of a general optical fiber connector.

FIG. 3 is a schematic view of a general optical fiber connector. The general optical fiber connector includes ferrules 302 made of ceramic, metal, or the like for protecting optical fibers 301, and fixing mechanisms such as a screw 303 for crimping the ferrule 302 through the optical fiber 301. The ferrules 302 pass through both ends of a cylindrical-shaped sleeve 304, and the ferrules 302 are crimped to the sleeve 304 by using the screws 303 to connect the fibers 301 to each other.

Figure 4:
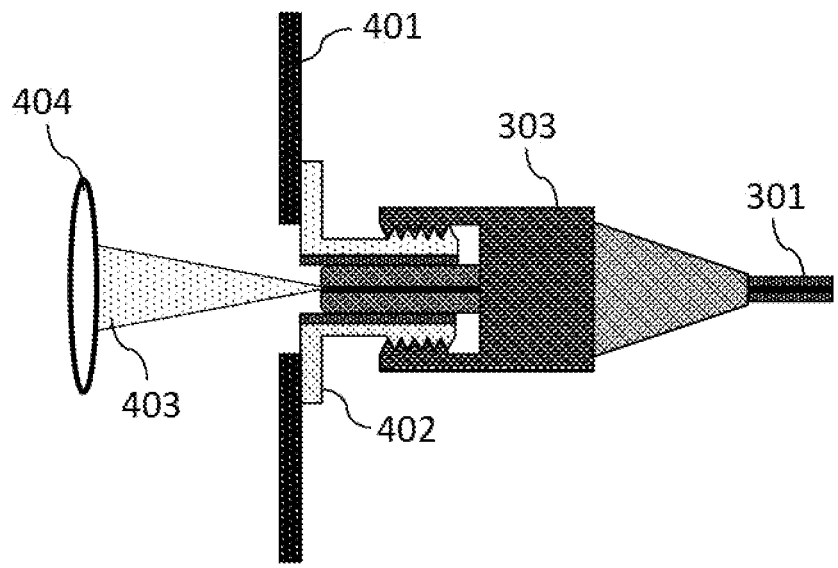
FIG. 4 is another example of an optical fiber connector.

FIG. 4 is another example of an optical fiber connector. FIG. 3 shows a case where the optical fibers are connected to each other from both sides of the optical fiber connector. On the contrary, when the laser light propagating in a space is converged and introduced inside the optical fiber, a mechanism similar to that in FIG. 3 may be used in order to be able to protect an end surface of the optical fiber and to remove the guidewire. In FIG. 4, as an example, a fixing metal fitting 402 is attached to a wall surface 401 of a light source unit, and the optical fiber connector is fixed to the fixing metal fitting 402. Laser light 403 is converged by a lens 404 to an end surface of the optical fiber 301, and the laser light is introduced from the end surface into the optical fiber 301.

On the other hand, it is considered that the optical fiber connector may be disposed at a tip end part of the guidewire, and the device and the guidewire may be connected by fitting the optical fiber connector to the ultrasonic imaging apparatus. In the case, the optical fiber connector shown in FIGS. 3 and 4 cannot be used since a restriction exists that is different from a general use as described below.

(First Restriction of Guidewire Connector)

The guidewire is an instrument as a guide for guiding an instrument, such as a catheter for another treatment examination. After the tip end portion of the guidewire reaches the affected portion, another catheter or the like is introduced along the wire from a base of the guidewire. The catheter is provided with a ring through which the wire is passed or the catheter itself is provided a lumen through which the wire is passed. Therefore, the optical fiber connector has to be smaller than the outer diameter of a guidewire body so as not to interfere with the introduction of another instrument.

(Second Restriction of Guidewire Connector)

It is necessary for the guidewire to be kept clean at all times during operation since the guidewire is a device inserted into the body. Therefore, the guidewire is generally sterilized and delivered to an operating room in a clean package. When used, the guidewire is treated in a manner of adhering only to blood of a subject undergoing treatment.

On the other hand, the ultrasonic imaging apparatus 101 and a laser body are not necessarily clean since they are used for many times. Therefore, when using a general optical fiber connector, when the guidewire is connected to the laser body, the distal end portion of the guidewire may become unclean. The cleanliness of another treatment instrument may also be impaired by the distal end portion of the guidewire whose cleanliness is impaired since another instrument is inserted from the distal end of guidewire.

It is noted that in PTL 2, cleanliness is kept. However, the technique of PTL 2 keeps cleanliness by providing a sterile barrier, and does not describe a requirement relating to an outer diameter of the optical fiber connector or a method for meeting the requirement.

First Embodiment

Figure 5:
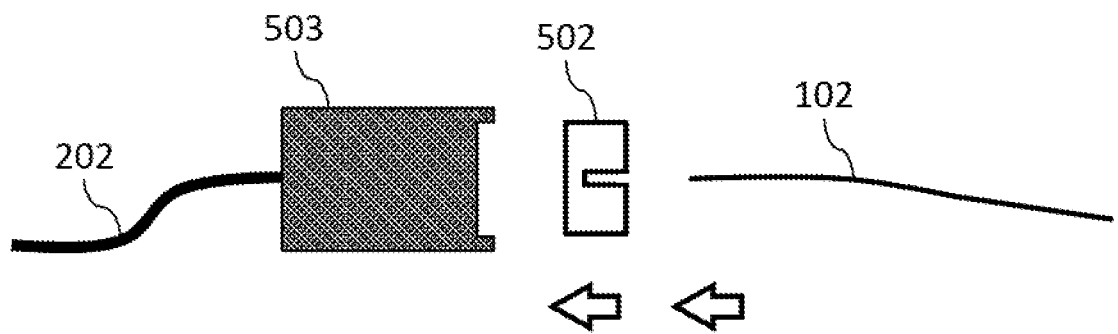
FIG. 5 is an overall schematic view of a guidewire connector according to a first embodiment.
Figure 5:
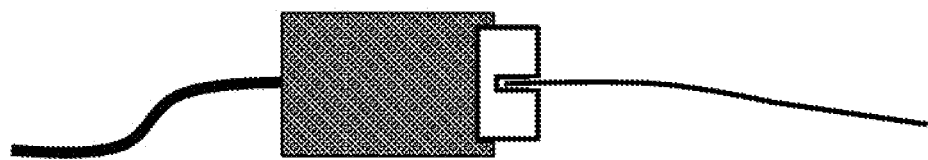

FIG. 5 is an overall schematic view of a guidewire connector according to the first embodiment of the disclosure. The guidewire connector includes an adapter unit 502. The adapter unit 502 can be detachably attached to the ultrasonic imaging apparatus 101. The guidewire 102 and the adapter unit 502 are disposable. A connection unit 503 is a member that connects the optical fiber 202 extending from the ultrasonic imaging apparatus 101 and the adapter unit 502. The connection unit 503 is a member on an ultrasonic imaging apparatus 101 side, and is not disposable. The laser light is guided from the laser light source to the connection unit 503 by the optical fiber 202. The adapter unit 502 is fixed to the connection unit 503, and the guidewire 102 is fixed to the adapter unit 502.

Figure 6:
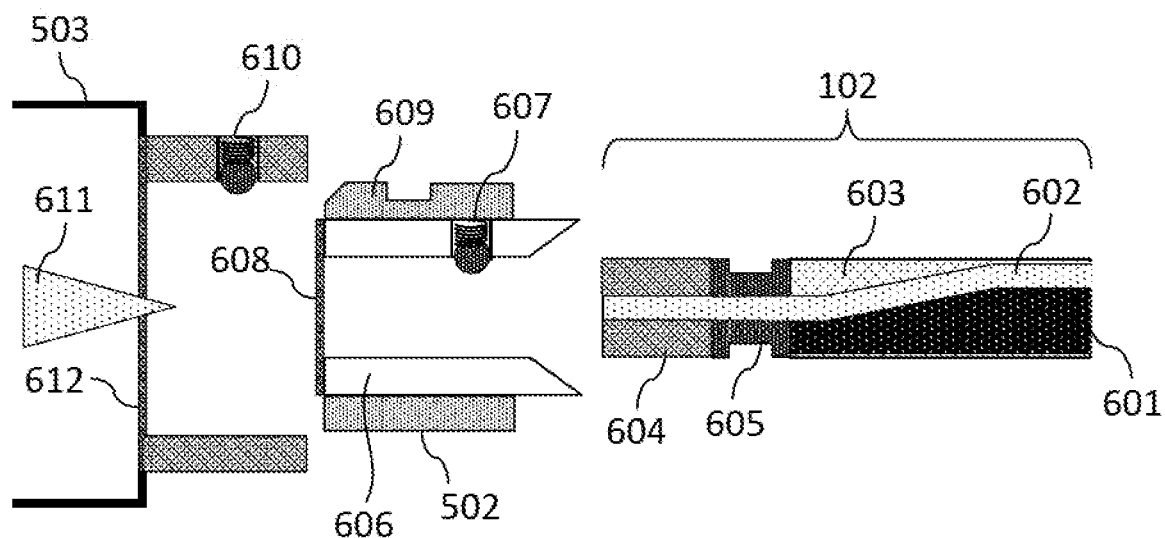
FIG. 6 is a cross-sectional view showing a detailed structure of the guidewire connector.
Figure 6:
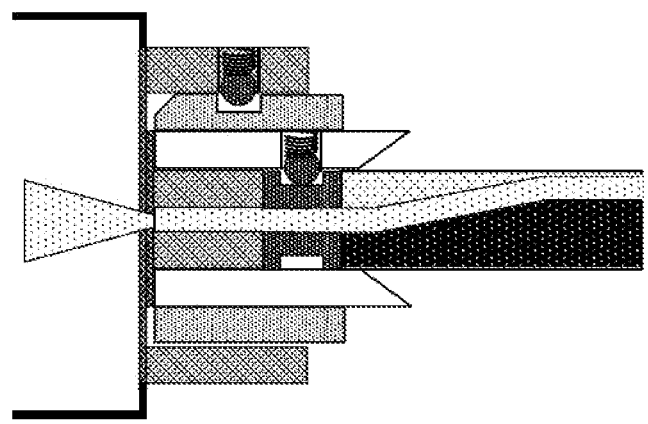

FIG. 6 is a cross-sectional view showing a detailed structure of the guidewire connector. The guidewire 102 is configured by disposing an optical fiber 602 along a metal wire 601. The metal wire 601 and the optical fiber 602 are coated with a coating agent 603. A ferrule 604 is provided at a distal end of the guidewire 102. A clasp 605 is provided adjacent to the ferrule 604. As shown in FIG. 6, the clasp 605 is provided with a recess. The clasp 605 has a cylindrical shape through which the optical fiber 602 passes.

The adapter unit 502 includes a sleeve 606 that receives the ferrule 604. The inside of the sleeve 606 includes a fixing mechanism 607 fitted to a groove of the clasp 605. For example, a hole or a groove is provided in the sleeve 606, and the fixing mechanism 607 is provided in the hole or the groove. The fixing mechanism 607 has, for example, a structure in which a sphere is fixed to a tip of a spring, and the guidewire 102 is fixed to the adapter unit 502 by fitting the ball into the recess of the clasp 605. At an end portion of the adapter unit 502, a glass plate 608 is provided for segregation to prevent the blood or the like adhering to the guidewire 102 from adhering to the connection unit 503. In the example, although the ferrule 604 and the clasp 605 have separate structures, the ferrule 604 may also function as the clasp 605 by being provided with a groove.

The adapter unit 502 includes a clasp 609 to be fixed to the connection unit 503. The adapter unit 502 is fixed to the connection unit 503 by fitting the clasp 609 to the fixing mechanism 610 provided in the connection unit 503. Different from the guidewire 102, there is no restriction on the diameter in the method of fixing the adapter unit 502 to the connection unit 503. Therefore, a structure other than that shown in FIG. 6 may be used. For example, in a method, the clasp 609 may be provided with a male screw, and may be fixed to a female screw provided in the connection unit 503.

When the guidewire 102 and the adapter unit 502 are fixed to the connection unit 503, the laser light 611 is converged toward a point where an end surface of the optical fiber 602 is positioned, and accordingly, the laser light 611 is introduced into the optical fiber 602. The connection unit 503 includes a transparent window 612 to prevent intrusion of dust and the like into the inside while the laser beam passes through.

When the guidewire 102 is inserted into the body, the guidewire 102 may be rotated about an axis (about an axis along a longitudinal direction of the guidewire 102) to adjust a travel direction. Therefore, the guidewire connector also needs to be made rotatable about the axis. In the example shown in FIG. 6, the clasp 605 has an axial object structure and the fixing mechanism 607 does not fix an axial rotation of the clasp 605. With such a mechanism, the guidewire 102 can be fixed in the longitudinal direction while maintaining a freedom degree of rotation about the axis. However, it is necessary for the optical fiber 602 to be provided at a center of a rotation axis such that the position of the optical fiber 602 does not deviate during rotation.

Although FIG. 6 shows an example in which the guidewire 102 rotates at a part connected to the adapter unit 502, the structure for ensuring the freedom degree of rotation is not necessarily limited to this shape. As an example, a bearing may be installed inside the adapter unit 502 such that the sleeve 606 is rotatable with respect to an outer frame of the adapter unit 502.

Figure 7:
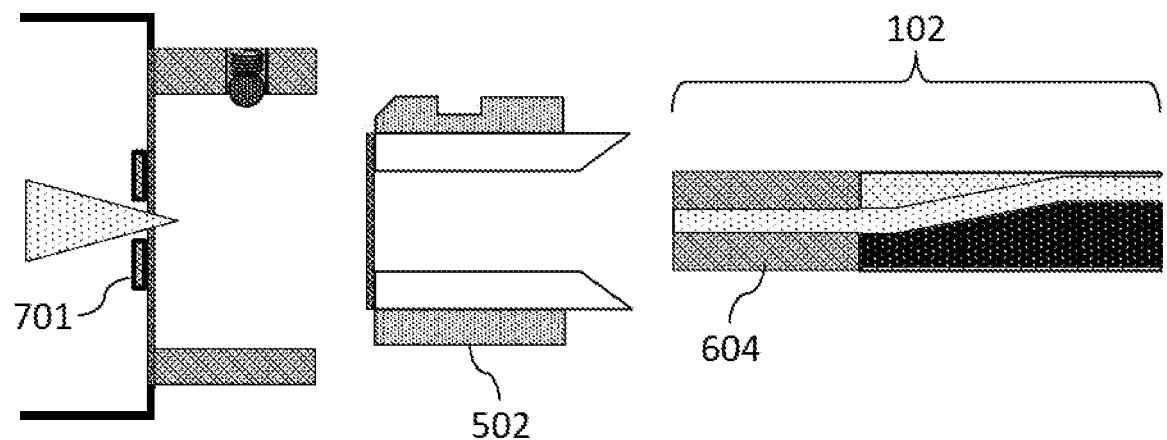
FIG. 7 is a diagram showing another configuration example of fixing a guidewire 102 to an adapter unit 502.
Figure 7:
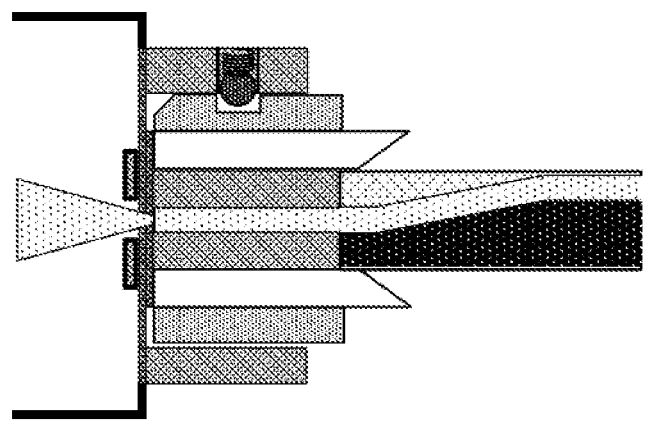

FIG. 7 is a diagram showing another configuration example of fixing the guidewire 102 to the adapter unit 502. The guidewire 102 is not necessarily fixed only by a mechanical holding mechanism. For example, the guidewire 102 may be fixed by a magnet as shown in FIG. 7. In the example of FIG. 7, the ferrule 604 contains a magnetic metal including iron or the like, and a magnet 701 is installed in the connection unit 503. The position in the longitudinal direction of the guidewire 102 is fixed when the ferrule 604 at the tip end is attracted to the magnet.

Figure 8:
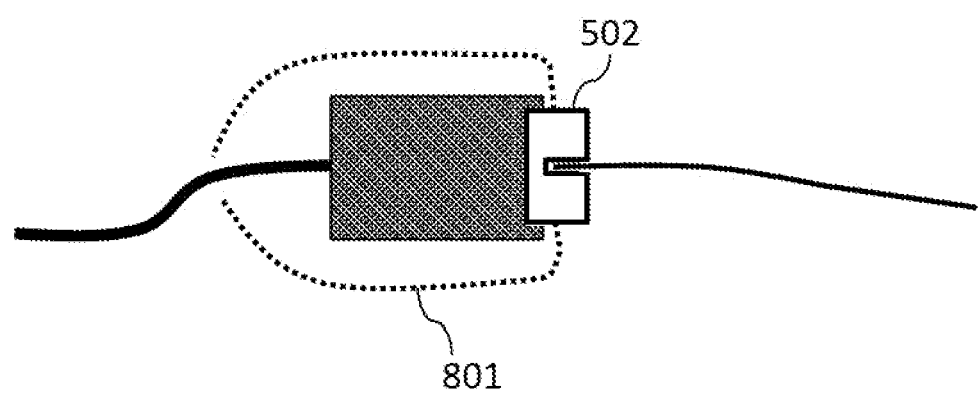
FIG. 8 is a configuration example for keeping cleanliness of the adapter unit 502.

FIG. 8 is a configuration example for keeping cleanliness of the adapter unit 502. It is considered that connection unit 503 may be placed near an area in which a surgery is being performed to facilitate operation after coupling the adapter unit 502 and the guidewire 102. In order to keep the cleanliness of the guidewire 102, it is necessary for the guidewire 102 to be installed in a clean area that has been sterilized to the distal end portion. However, the connection unit 503 is not disposable, and cleanliness is not ensured. In order to solve the problem, a clean bag 801 such as vinyl is provided on the adapter unit 502. When in use, a periphery of the connection unit 503 is covered with the bag 801 to prevent a part where cleanliness is not ensured from touching a clean part.

Figure 9:
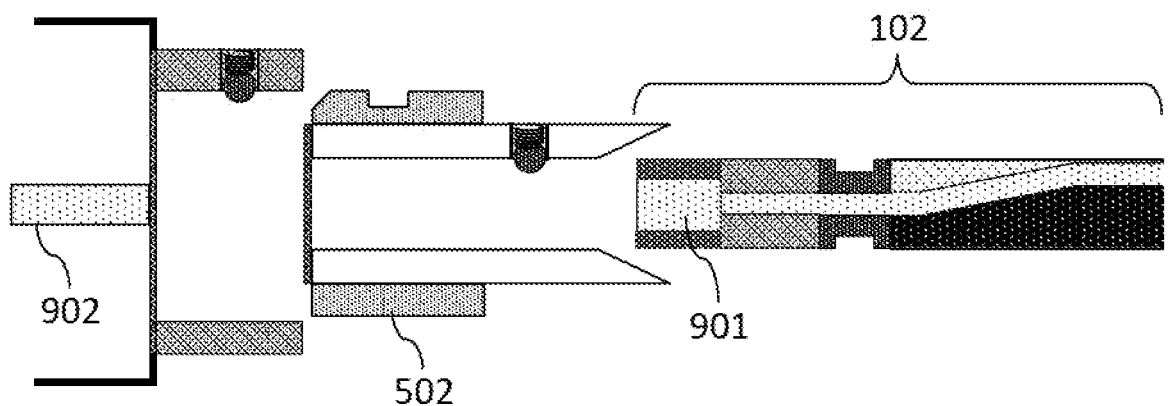
FIG. 9 is a configuration example of inhibiting a position deviation of laser light.
Figure 9:
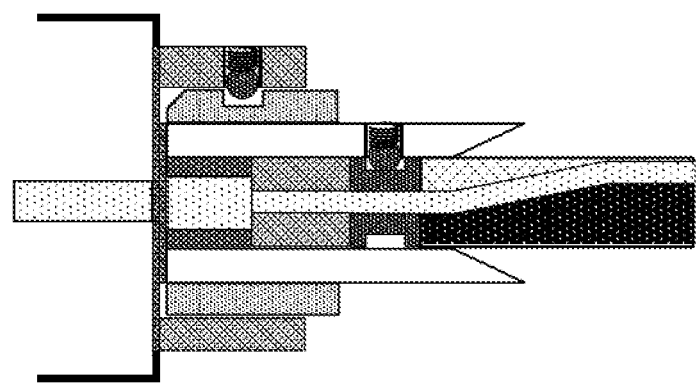

FIG. 9 is a configuration example of inhibiting position deviation of the laser light. The laser light 611 is converged to a distal end portion of the optical fiber 602 for introducing the laser light inside the optical fiber 602. On the other hand, a diameter of a core of a general optical fiber (a portion that propagates laser light) is about 10 to 100 Therefore, it is necessary for the position deviation of the converged laser light with respect to the optical fiber 602 to be equal to or less than the above degree. In order to prevent deviation of the position of the laser light 611 with respective to the optical fiber 602, fixing accuracy of the adapter unit 502 to the guidewire 102 needs to be in an equal or higher degree. Such a limitation on the positional deviation can be alleviated by providing, for example, a lens on the guidewire 102.

For example, a rod lens 901 such as a GRIN lens is provided at the distal end of the guidewire 102. In the case, the laser light 902 is not converged and is incident on the guidewire 102 while maintaining as parallel light, converged by the rod lens 901, and introduced into the optical fiber 602. Since the amount of positional deviation of a converging point of the laser light 902 with respect to the optical fiber 602 is smaller than the amount of positional deviation of the adapter unit 502 and the guidewire 102, a requirement for the fixing accuracy of the adapter unit 502 to the guidewire 102 is alleviated. The rod lens 901 is not necessarily fixed to the tip end of the guidewire 102, and may be fixed to the sleeve 606.

Figure 10:
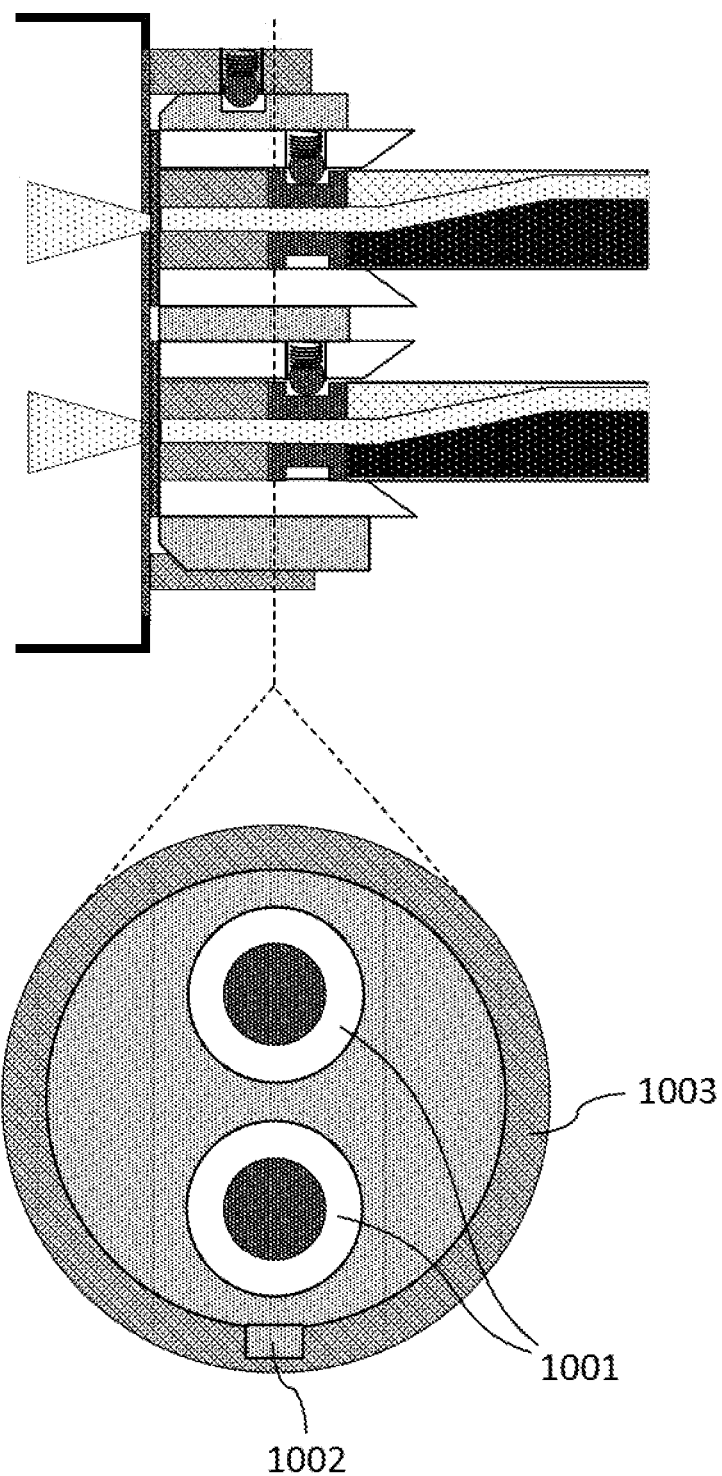
FIG. 10 is a configuration example in which a plurality of guidewires 102 are connected to the adapter unit 502.

FIG. 10 is a configuration example in which a plurality of guidewires 102 are connected to the adapter unit 502. Although an example in which one guidewire 102 is connected to the laser light source is shown in the above description, the plurality of guidewires 102 may be used in parallel in the treatment. In order to cope with such a case, the adapter unit 502 may include a plurality of connection ports 1001 for connection of the guidewires as shown in FIG. 10. In the case, in order to align the position of the laser light and the position of the optical fiber 602, a rotational position about the axis of the adapter unit 502 must be fixed to the connection unit 503. Specifically, for example, as shown in a front view of the adapter unit 502 on a lower side of FIG. 10, a protrusion portion 1002 for fixing a rotation direction is fitted into a groove provided in the fixing mechanism 1003 of the adapter unit 502 provided in the connection unit 503. With such a structure, the rotational position of the adapter unit 502 can be fixed.

Figure 11:
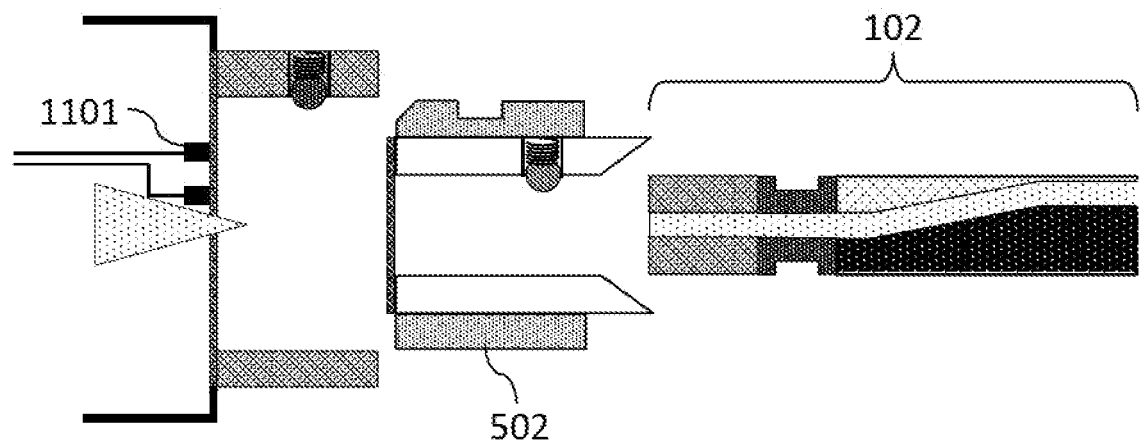
FIG. 11 is a configuration example of limiting irradiation of laser light.

FIG. 11 is a configuration example of limiting irradiation of the laser light. From a viewpoint of safety, it is desirable to irradiate the guidewire 102 with laser light only when the adapter unit 502 and the guidewire 102 are fixed to the connection unit 503 such that the laser light does not leak to an outside. As an example, as shown in FIG. 11, two proximity sensors 1101 are provided in the connection unit 503. Each sensor detects an object when the guidewire 102 approaches the sensor and when the adapter unit 502 approaches the sensor. The proximity sensors 1101 outputs a detection result to the light source unit. The light source unit irradiates laser light only when both of the two sensors detect a proximity object. Accordingly, the laser light can be prevented from leaking to the outside. Instead of blocking the laser light by the light source unit, a shutter that blocks the laser light may be provided when any one of the proximity sensors does not detect the proximity object.

The guidewire 102 may adhere blood of the subject at the distal end portion thereof during a process of treatment. Since the adhered blood may cause a loss of the laser light, the adapter unit 502 may be provided with a fabric for applying a water-repellent coating at the distal end portion of the guidewire 102 or cleaning the distal end portion of the wire at the time of connection to avoid the loss.

First Embodiment: Summary

The guidewire connector according to the first embodiment includes the adapter unit 502 detachable to the ultrasonic imaging apparatus 101, and fixes the guidewire 102 to the adapter unit 502. Accordingly, the cleanliness of the guidewire 102 can be kept since the adapter unit 502 and the guidewire 102 can be used as disposable members.

In the guidewire connector according to the first embodiment, the outer diameter of the clasp 605 is smaller than the outer diameter of the guidewire 102. Therefore, the clasp 605 does not inhibit an introduction of another instrument when the other instrument such as catheter is introduced along the guidewire 102. Accordingly, the guidewire 102 can be fixed without inhibiting the introduction of the other instrument.

Second Embodiment

Figure 12:
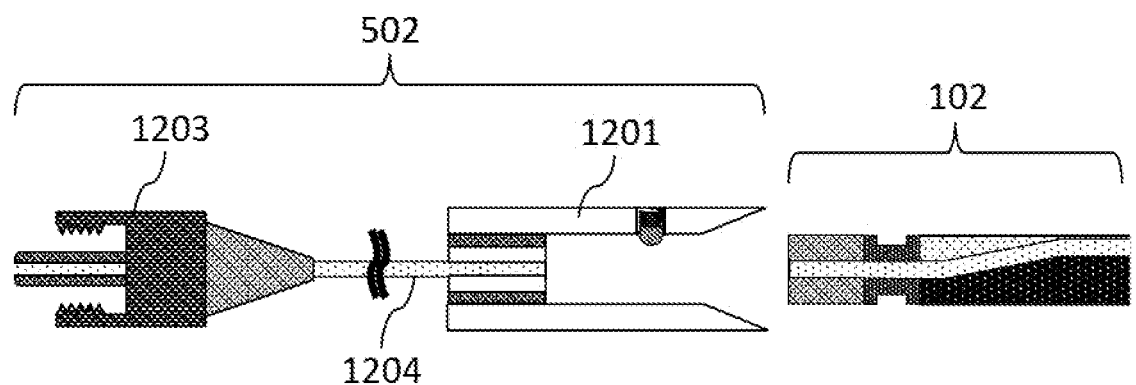
FIG. 12 is a cross-sectional side view showing a structure of a guidewire connector according to a second embodiment.
Figure 12:
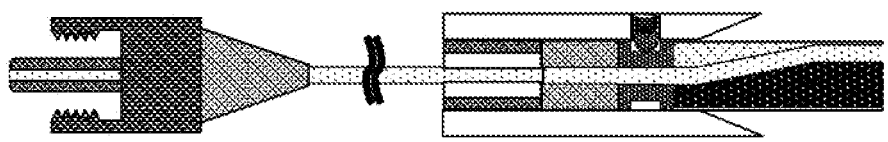

FIG. 12 is a cross-sectional side view showing a structure of a guidewire connector according to the second embodiment. The adapter unit 502 in the second embodiment has a cable-shaped structure whose entire length is extended by the optical fiber 1204. The adapter unit 502 in the second embodiment includes a connection unit 1201, an optical fiber 1204, and an optical fiber connector 1203. One end of the connection unit 1201 is connected to the guidewire 102. The other end of the connection unit 1201 is connected to the optical fiber 1204. The adapter unit 502 and the ultrasonic imaging apparatus 101 are connected by fitting the optical fiber connector 1203 to a similar optical fiber connector provided in the ultrasonic imaging apparatus 101.

Although the laser light is converged at the end of the adapter unit 502 in the first embodiment, the laser light is introduced to the connection unit 1201 by the optical fiber 1204 in the second embodiment. Similar as in the first embodiment, a lens may be provided at the tip end portion of the guidewire 12 in order to alleviate the restriction on positional accuracy at the time of connection.

A function of the connection unit 1201 is similar to that in the first embodiment. As an example, the guidewire 102 is fixed by fitting a groove and a clasp provided in the guidewire 102. Similar as in the first embodiment, the guidewire 102 is rotatable around the central axis. A fixing method is not necessarily limited to a mechanical method, and it is also possible to adopt another method such as magnetic fixing as in FIG. 7. In the example shown in FIG. 12, the structure of the connection between the guidewire 102 and the adapter unit 502 enables the rotation as described in the first embodiment. The structure for ensuring the freedom degree of rotation of the guidewire 102 is not necessarily limited to the shape shown in FIG. 12. As an example, as in the first embodiment, the guidewire 102 may be rotatable by installing a bearing inside the connection unit 1201, fixing the optical cable 1202 to a bearing outer frame and fixing the sleeve 606 to a bearing inner side.

Since there is no restriction on the outer diameter of the optical fiber connector 1203, a general optical fiber connector may be used. However, from the viewpoint of cleanliness, it is desirable that the optical fiber connector 1203 can be connected while only the optical fiber connector 1203 is held by a hand without touching an unsterilized part such as the connection unit 503. It is desirable that the adapter unit 502 is entirely sterilized from the viewpoint of cleanliness.

Also in the second embodiment, as in the first embodiment, it is desirable that sensors for detecting the connection are provided such that the laser light is irradiated only when both the adapter unit 502 and the guidewire 102 are connected to the connection unit 503 from the viewpoint of safety. As in the first embodiment, a bag or the like for separating a clean area and a non-clean area may be provided.

Figure 13:
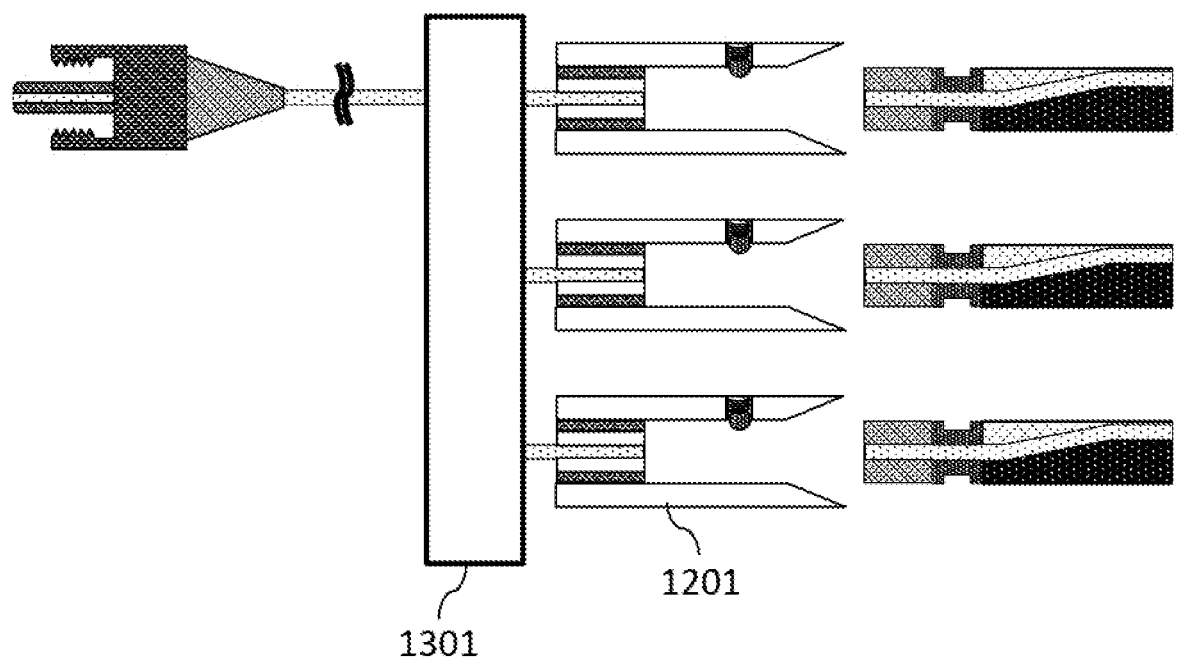
FIG. 13 is a configuration example in which the plurality of guidewires 102 are connected.

FIG. 13 is a configuration example in which the plurality of guidewires 102 are connected. Also in the second embodiment, the plurality of guidewires may be connectable as in the first embodiment. As an example, as shown in FIG. 13, an optical splitter 1301 is provided between the optical fiber connector 1203 and the optical fiber 1204, and a plurality of connection units 1201 are provided in a subsequent part. The optical splitter 1301 splits a laser beam supplied from an optical fiber connector 1203 side by a beam splitter or the like, and distributes the laser beam to each optical fiber 1204 in the subsequent part. With such a structure, the plurality of guidewires can be used at the same time.

<Modification of Disclosure>

The disclosure is not limited to the embodiments described above, and includes various modifications. For example, the above-described embodiments have been described in detail for easy understanding of the disclosure, and are not necessarily limited to those having all the configurations described above. A part of the configuration of a certain embodiment can be replaced with the configuration of another embodiment, and the configuration of another embodiment can be added to the configuration of a certain embodiment. A part of the configuration of each embodiment can be added, deleted, or replaced with another configuration.

In the above embodiments, although the example in which the optical fiber 602 is accommodated inside the guidewire 102 is shown, the position of the optical fiber 602 is not limited thereto. For example, the disclosure can be applied when the optical fiber 602 is provided along the guidewire 102. That is, even in this case, it is desirable that the outer diameter of the clasp 605 is set to be equal to or smaller than the outer diameter of the guidewire 102.

The above embodiments have described an example in which it is assumed that the catheter is guided along the guidewire 102 when the catheter is introduced in the body. The in-body insertion instrument guided by the guidewire 102 is not limited to a catheter, and the disclosure can be applied to a case where other in-body insertion instruments are guided.

What is claimed is:

1. A guidewire connector that connects an apparatus configured to emit light and a guidewire configured to guide an in-body insertion instrument, in which
a first optical fiber that receives the light is disposed along the guidewire,
the guidewire connector comprising:
an adapter member detachably attached to the apparatus; and
a wire fixing member configured to fix the guidewire to the adapter member, wherein
the wire fixing member has an outer diameter equal to or smaller than an outer diameter of the guidewire.

2. The guidewire connector according to claim 1, wherein
the adapter member includes a first hollow portion into which the guidewire is inserted,
the wire fixing member includes a first fixing mechanism protruding from an inner wall of the adapter member toward the first hollow portion, and
an inner diameter of the first hollow portion defined by the inner wall of the adapter member and a tip end of the first fixing mechanism is equal to or smaller than an outer diameter of the guidewire.

3. The guidewire connector according to claim 2, wherein
the wire fixing member includes a clasp having a second hollow portion through which the first optical fiber passes,
the clasp has a recess to be fitted with the first fixing mechanism, and
an outer diameter of the recess is equal to or smaller than the outer diameter of the guidewire.

4. The guidewire connector according to claim 3, wherein
the first fixing mechanism includes an elastic member protruding from an inner wall of the wire fixing member toward the first hollow portion, and
when the guidewire is inserted into the first hollow portion, the elastic member fixes the guidewire to the adapter member by pressing the first fixing mechanism to the recess in accordance with elastic force.

5. The guidewire connector according to claim 3, wherein
the recess is formed so as to be rotationally symmetric about a rotation axis extending along a longitudinal direction of the guidewire, and
the wire fixing member fixes the guidewire such that the guidewire can be rotated along the rotation axis by fitting the first fixing mechanism and the recess.

6. The guidewire connector according to claim 1, wherein
the wire fixing member fixes the guidewire such that the guidewire can be rotated along a rotation axis extending along a longitudinal direction of the guidewire.

7. The guidewire connector according to claim 1, wherein
the wire fixing member is configured using a magnetic material that fixes the guidewire to the adapter member by magnetic force.

8. The guidewire connector according to claim 1, wherein
the adapter member includes a bag configured to avoid contact between a non-clean site and a clean site.

9. The guidewire connector according to claim 1, further comprising:
a lens configured to converge the light to a light introducing end of the first optical fiber.

10. The guidewire connector according to claim 1, wherein
the wire fixing member is configured to be capable of fixing two of the guidewires or more to the adapter member respectively, and
the adapter member includes a second fixing mechanism configured to fix a rotational position of the adapter member to the apparatus.

11. The guidewire connector according to claim 1, wherein the adapter member includes
a second optical fiber configured to propagate the light, and
an optical fiber connector connecting the second optical fiber to the apparatus, wherein
the optical fiber connector is configured to be detachable to the apparatus.

12. The guidewire connector according to claim 11, wherein
the apparatus is configured to emit the light from two of the second optical fibers or more branched via an optical branching unit, and
the wire fixing member is configured such that, for each of the second optical fibers, another guidewire can be fixed to the adapter member.

13. An ultrasonic imaging apparatus configured to capture an image of a subject using an ultrasonic wave, the ultrasonic imaging apparatus comprising:
an ultrasonic oscillator formed of a light absorbing material that is configured to transmit the ultrasonic wave by absorbing light;
an ultrasonic probe configured to receive a reflected ultrasonic wave reflected from the subject;
an image generation unit configured to generate an ultrasonic image of the subject using the reflected ultrasonic wave received by the ultrasonic probe;
a light source configured to supply the light to the ultrasonic oscillator; and
a guidewire connector connecting the ultrasonic imaging apparatus and a guidewire configured to guide an in-body insertion instrument, wherein a first optical fiber that receives the light is disposed along the guidewire, and the guidewire connector includes
an adapter member detachably attached to the ultrasonic imaging apparatus, and
a wire fixing member fixing the guidewire to the adapter member, wherein
the wire fixing member has an outer diameter equal to or smaller than an outer diameter of the guidewire.

14. The ultrasonic imaging apparatus according to claim 13, further comprising:
a sensor configured to detect whether the adapter member is attached to the ultrasonic imaging apparatus and detect whether the guidewire is attached to the adapter member; and
a blocking unit configured to block the light when the sensor detects that the adapter member is not attached to the ultrasonic imaging apparatus, or the guidewire is not attached to the adapter member.

* * * * *